US011634385B2

(12) United States Patent
Ott et al.

(10) Patent No.: US 11,634,385 B2
(45) Date of Patent: Apr. 25, 2023

(54) PROCESS FOR THE PREPARATION OF HALOALKANESULFONIC ACIDS FROM SULFUR TRIOXIDE AND A HALOALKANE

(71) Applicant: GRILLO-WERKE AG, Duisburg (DE)

(72) Inventors: Timo Ott, Duisburg (DE); Christian Diaz-Urrutia, Ontario (CA); Ingo Biertuempel, Duisburg (DE)

(73) Assignee: Grillo-Werke AG, Duisburg (DE)

( * ) Notice: Subject to any disclaimer, the term of this patent is extended or adjusted under 35 U.S.C. 154(b) by 78 days.

(21) Appl. No.: 17/054,630

(22) PCT Filed: May 23, 2019

(86) PCT No.: PCT/EP2019/063337
§ 371 (c)(1),
(2) Date: Nov. 11, 2020

(87) PCT Pub. No.: WO2019/224311
PCT Pub. Date: Nov. 28, 2019

(65) Prior Publication Data
US 2021/0070700 A1 Mar. 11, 2021

(30) Foreign Application Priority Data
May 25, 2018 (EP) .................................. 18174283

(51) Int. Cl.
C07C 303/06 (2006.01)
C07C 305/26 (2006.01)
(52) U.S. Cl.
CPC .......... *C07C 303/06* (2013.01); *C07C 305/26* (2013.01)
(58) Field of Classification Search
CPC ... C07C 303/06; C07C 305/26; C07C 309/04; C07C 303/42; B01J 31/02; C12N 2501/999; C12N 5/0609; G05D 1/0088; G06N 3/0454; G06N 3/08; H04W 4/40
See application file for complete search history.

(56) References Cited

U.S. PATENT DOCUMENTS 10,329,251 B2    6/2019  Ott et al.
2006/0100458 A1* 5/2006  Sen .................. C07C 303/02
                                                562/98

FOREIGN PATENT DOCUMENTS

CN      105705486 A       6/2016
WO      2015071455 A1     5/2015
WO   WO-2015071455 A1 *   5/2015 ........... C07C 303/06

OTHER PUBLICATIONS

Mukhopadhyay et al. (Synthesis of Trifluoromethanesulfonic Acid from CHF3, Organic Process Research & Development, vol. 8, pp. 660-662, Published Nov. 2004. Cited in the IDS filed Nov. 11, 2020) (Year: 2004).*
Mukhopadhyay et al. 2003 (A High-Yield Approach to the Sulfonation of Methane to methanesulfonic Acid Initiated by H2O2 and a Metal Chloride, Communications, Angew. Chem. Int. Ed. 42, pp. 2990-2993) (Year: 2003).*
Mukhopadhyay, S., et al., "Synthesis o, No. 4f Trifluoromethanesulfonic Acid from CHF3", Organic Process Research & Development, Nov. 6, 2004, pp. 660-662, vol. 8.
Prakash, G.K.S., et al., "Taming of Fluoroform: Direct Nucleophilic Trifluoromethylation of Si, B, S, and C Centers", Science, Dec. 7, 2012, p. 1324-1327, vol. 338, No. 6112.
International Search Report and Written Opinion dated Aug. 7, 2020, prepared in International Application No. PCT/EP2019/063337.

* cited by examiner

*Primary Examiner* — Jafar F Parsa
*Assistant Examiner* — Blaine G Doletski
(74) *Attorney, Agent, or Firm* — Barnes & Thornburg LLP

(57) ABSTRACT

The present invention relates to a process for preparing haloalkanesulfonic acids from sulfur trioxide and a haloalkane, particularly to a process for preparing trifluoromethane sulfonic acid from sulfur trioxide and trifluoromethane.

23 Claims, No Drawings

PROCESS FOR THE PREPARATION OF HALOALKANESULFONIC ACIDS FROM SULFUR TRIOXIDE AND A HALOALKANE

This application is a National Stage application of International Application No. PCT/EP2019/063337, filed May 23, 2019. This application also claims priority under 35 U.S.C. § 119 to European Patent Application No. 18174283.4, filed May 25, 2018. Each of these references is hereby incorporated by reference in its entirety.

The present invention relates to a process for preparing haloalkanesulfonic acids from sulfur trioxide and a haloalkane, particularly to a process for preparing trifluoromethane sulfonic acid from sulfur trioxide and trifluoromethane.

Haloalkanes, also known as halogenalkanes or alkyl halides, are a group of chemical compounds structurally derived from alkanes by replacing one or more hydrogen atoms by halogen atoms. They are widely used as flame retardants, fire extinguishants, refrigerants, propellants, solvents and pharmaceuticals. By replacing a hydrogen atom of a haloalkane by a sulfonic acid group $SO_3H$, haloalkanesulfonic acids can be derived. Said haloalkanesulfonic acids are also formally derivable from alkanesulfonic acids by replacing hydrogen atoms by halogen atoms.

Among the haloalkanesulfonic acids, trifluoromethanesulfonic acid (TFMS), which is also known as triflic acid and has the chemical formula $CF_3SO_3H$, is of particular technical importance. At room temperature TFMS is a hygroscopic, clear and colorless liquid, soluble in polar solvents. Notably, TFMS is a super acid and with a pKa value of −14.7 one of the strongest known acids. Trifluoromethansulfonic acid is widely used as a catalyst for esterification, and isomerization, among other reactions. Triflic acid's conjugate base $CF_3SO_3—$ is called triflate and is a well-known protection group in organic chemistry. On an industrial scale, trifluoromethanesulfonic acid is particularly used in the polymer, fuel, pharmaceutical and sugar industry.

On an industrial scale, trifluoromethanesulfonic acid is produced by electrochemical fluorination of methanesulfonic acid (T. Gramstad and R. N. Haszeldine, J. Chem. Soc., 1956, 173). In theory, trifluoromethanesulfonic acid could also be prepared by the direct reaction of trifluoromethane ($CF_3H$) and sulfur trioxide.

$CF_3H$ is a strong greenhouse gas with a global warming potential of 15,000 times more than one molecule of carbon dioxide. It was formerly used as a refrigerant, although this application should now be avoided. Trifluoromethane is still produced, however, as an undesirable side-product in a number of industrial processes, e.g., in the production of polytetrafluoroethylene (PTFE), also known as teflon. There is thus need to eliminate excess trifluoromethane, preferably by transforming it into some useful and harmless substance. The reaction with sulfur trioxide might yield TFMS, which is considered to be an environmentally friendly acid.

Mukhopadhyay et al. (S. Mukhopadhyay, A. T. Bell, R. V. Srinivas, G. S. Smith, Org. Proc. Res. Dev. 2004, 8, 660) describe the direct synthesis of trifluoromethanesulfonic acid from trifluoromethane and sulfur trioxide employing hydrogen peroxide-urea and $RhCl_3$ as catalyst in fuming sulfuric acid. The yield, however, is small and the method is not economically feasible.

Therefore, there is still need for a process, which can transform trifluoromethane to trifluoromethanesulfonic acid in an efficient and economically feasible way. Such a process could provide both an efficient route to trifluoromethanesulfonic acid and a new method to eliminate trifluoromethane by converting it to a useful and harmless substance.

It is thus the object of the present invention to provide an improved process for the preparation of haloalkanesulfonic acids from the respective haloalkane and sulfur trioxide. Particularly, a process for the preparation of trifluoromethanesulfonic acid from trifluoromethane and sulfur trioxide should be provided.

In a first embodiment, the object of the present invention is solved by the use of a compound comprising at least one peroxoacid or a salt thereof, wherein the peroxoacid is stable at room temperature, as a catalyst in the preparation of haloalkanesulfonic acids from haloalkanes and sulfur trioxide, especially in the preparation of trifluoromethanesulfonic acid from trifluoromethane and sulfur trioxide. Particularly, fluorinated, chlorinated and brominated derivatives of methane, ethane, propane, butane, isopropane, isobutane or a higher alkane can react with sulfur trioxide to form the corresponding haloalkanesulfonic acid.

Higher alkane within the meaning of the present invention refers to a branched or unbranched alkane with a carbon number of 2 to 20.

Stability at room temperature is particularly to be understood as the stability in a reaction solvent comprising sulfur trioxide and a haloalkane, especially trifluoromethane. This solvent may be sulfuric acid. The peroxoacid according to the invention must be stable enough in order to act as catalyst in the production of haloalkanesulfonic acids and not to decompose.

Said decomposition may particularly take place by the release of reactive oxygen species such as superoxide anions ($O_2^-$) and/or molecular oxygen. In this sense, stability of the peroxoacid catalysts of the present invention for example means the absence of the release of reactive oxygen species such as superoxide anions and/or molecular oxygen.

According to the invention, the peroxoacid is used as a catalyst in a condensed-phase homogeneous process. The peroxoacid catalyst is dissolved in the same phase as the reactants, i.e., a haloalkane and sulfur trioxide.

In the following, the assumed catalytic cycle is exemplary described for the employment of trifluoromethane as haloalkane. The same catalytic cycle is assumed to apply to other haloalkanes. In general, the peroxoacid according to the invention can be described by the formula R—O—O—H. Without the intention of being bound by theory, it is assumed that the peroxoacid acts by activating sulfur trioxide towards the reaction with a haloalkane.

In a first step, the peroxoacid reacts with sulfur trioxide upon which an activated form of sulfur trioxide is formed:

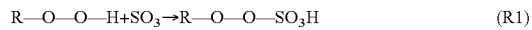

$$R—O—O—H + SO_3 \rightarrow R—O—O—SO_3H \quad (R1)$$

In a second step, said activated form is able to react with trifluoromethane in order to form trifluoromethanesulfonic acid upon which the peroxoacid is regenerated:

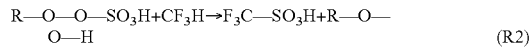

$$R—O—O—SO_3H + CF_3H \rightarrow F_3C—SO_3H + R—O—O—H \quad (R2)$$

In a preferred embodiment, the peroxoacid comprises at least one compound of formula (I)

$$ALK-SO_2—O—O—X, \quad (I)$$

wherein ALK is a branched or unbranched alkyl group, especially a methyl, ethyl, propyl, butyl, isopropyl, isobutyl group, or a higher alkyl group, wherein the alkyl group may optionally be halogenated, and X=hydrogen, zinc, aluminium, an alkali or alkaline earth metal. For example, the compound of formula (I) with X=H can be manufactured by a process comprising reacting alkanesulfonic acids, especially methanesulfonic acid, with hydrogen peroxide. A compound of formula (I) may also be manufactured by a process comprising reacting haloalkanesulfonic acids, especially trifluoromethanesulfonic acid, with hydrogen peroxide. The obtained compound might be isolated but will preferably be used as initiator-precursor without any further isolation and/or cleaning step.

In particular, the isolation can be effected by extraction, chromatography, precipitation, recrystallization, freeze-drying or similar methods under mild conditions. In a particular embodiment of the process according to the invention, the isolation can be effected by means of precipitation or chromatography. Inert support materials and inert solvents, such as sulfuric or sulfonic acids, are employed therein. The use of organic solvents is also possible.

Inert support materials used for isolation are in particular those which do not negatively interfere with components being the actual reaction partners, e.g. by reducing the yield of the compound of the invention. Furthermore, inert support materials can either chemisorb or physisorb—or both—a chemical compound, without destroying its functionality or structure in an irreversible way. Examples are materials based on e.g. silicon dioxide, aluminium oxide, zirconium oxide and the like.

In an alternative embodiment, an inorganic peroxoacid is employed as peroxoacid. It has been found that stable inorganic peroxoacids show a similar catalytic activity as the peroxoacids derived from alkanesulfonic acids of formula (I). In principal, any inorganic peroxoacid, which is stable at room temperature, can be employed. Such inorganic peroxoacids or their corresponding oxoacids are cheaply available from commercial distributors.

In a preferred embodiment the peroxoacid comprises at least one peroxoacid of boron, silicon, phosphorus, carbon, nitrogen or sulfur. Any suitable peroxoacid of said elements can be used. The peroxoacids are typically derived from the corresponding oxoacid of the respective element.

Preferably, the peroxoacid used as a catalyst according to the invention is obtainable by a reaction of the corresponding oxoacid with a peroxide. More preferably, the peroxoacid is obtainable by a reaction of the corresponding oxoacid with hydrogen peroxide. Without the intention of being bound by theory, the reaction of an oxoacid with hydrogen peroxide can be described for example by

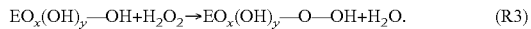

$$EO_x(OH)_y\text{—OH} + H_2O_2 \rightarrow EO_x(OH)_y\text{—O—OH} + H_2O. \qquad (R3)$$

In a preferred embodiment, the peroxoacid used according to the invention comprises a polyprotic acid. Particularly, the peroxoacid may consist of one or more polyprotic acids. Said polyprotic peroxoacid comprises one or more peroxy groups, which can be described by —O—O—X, wherein X may be hydrogen and/or an alkaline and/or alkaline-earth metal. More preferably X is hydrogen, lithium, sodium and/or potassium. Most preferably, X is hydrogen.

Preferably, if a polyprotic acid is used, the peroxoacid comprises one or more hydroxyl groups in addition to the one or more peroxy groups. Said hydroxyl groups may be present in form of a salt, i.e., the groups can be described by —O—X, wherein X may be hydrogen, an alkaline metal and/or an alkaline-earth metal. Most preferably X is hydrogen. The replacement of hydrogen with an alkaline-(earth) metal, however, may be particularly necessary to stabilize the peroxoacid as required by the invention.

In a preferred embodiment of the invention, the reaction product of phosphoric acid ($H_3PO_4$) with hydrogen peroxide, the reaction product of boric acid ($H_3BO_3$) with hydrogen peroxide and/or potassium peroxomonosulfate ($KHSO_5$) is used as stable inorganic peroxoacid according to the invention. Surprisingly, it has been found that said preferred peroxoacids are particularly suitable as catalyst in the preparation of haloalkanesulfonic acids from haloalkanes and sulfur trioxide.

In a preferred embodiment, any of the aforementioned peroxoacid catalysts can be used in addition with a compound M-R, wherein M is a metal, preferable a transition metal, particularly a first row transition metal, with an oxidation state of +1 to +7, and R is —H, —OH, —CH$_3$, —O—CH$_3$, —F, —Cl, —Br, —C$_2$H$_5$ or a higher alkyl group, —OC$_2$H$_5$ or a higher alkoxy group, or a suitable inorganic counter anion. Particularly metal salts such as CuCl, NiSO$_4$, CoCl$_2$, MnCl$_2$ or VCl$_2$ are preferred.

In the inventive use of a peroxoacid as catalyst, an initiator as activated form of sulfur trioxide is believed to be formed according to equation (R1). Although it is preferred to form said initiator in situ by introducing a peroxoacid into the reaction mixture, said initiator can also by produced separately. In an alternative embodiment, the object of the invention is thus solved by the use of an initiator comprising at least one compound of formula (II)

$$R\text{—O—O—SO}_2\text{—OX} \qquad (II)$$

wherein X is hydrogen, zinc, aluminum, an alkali or alkaline-earth metal, as a catalyst in the preparation of haloalkanesulfonic acids from haloalkanes and sulfur trioxide, especially in the preparation of trifluoromethanesulfonic acid from trifluoromethane and sulfur trioxide.

In this alternative embodiment, the activated form of sulfur trioxide corresponding to formula (II), which is believed to be formed by the reaction of the inventive peroxoacid with sulfur trioxide according to equation (R1), may be produced separately and introduced into the reaction mixture. The same catalytic cycle of (R1) and (R2) applies, but it is started from a different point, i.e. (R2) occurs after (R1).

Preferably, the initiator comprises at least one compound of formula (III)

$$ALK\text{-SO}_2\text{—O—O—SO}_2\text{—OX} \qquad (III),$$

wherein ALK is a branched or unbranched alkyl group, especially a methyl, ethyl, propyl, butyl, isopropyl, isobutyl group, or a higher alkyl group, wherein the alkyl group may optionally be halogenated, and X=hydrogen, zinc, aluminum, an alkali or alkaline-earth metal. This embodiment corresponds to the use of a peroxoacid derived from an alkanesulfonic acid or a haloalkanesulfonic acid as catalyst, wherein the activated form of sulfur trioxide according to (R1) is produced separately and introduced into the reaction mixture.

In a preferred embodiment, the initiator is obtainable by the reaction of a peroxoacid or a salt thereof, wherein the peroxoacid is stable at room temperature, with sulfur trioxide. Particularly peroxoacids derived from alkanesulfonic acids are suitable peroxoacids. Peroxoacids corresponding to formula (I) are also suitable peroxoacids.

In a preferred embodiment, the initiator is obtainable by the reaction of an inorganic peroxoacid or a salt thereof, wherein the peroxoacid is stable at room temperature, with sulfur trioxide. Particularly preferred inorganic peroxoacids are peroxoacids of boron, silicon, phosphorus or sulfur. Any of the above described peroxoacids, which may be used as catalyst, are suitable.

In a preferred embodiment, any of the aforementioned initiators can be used in addition with a compound M-R, wherein M is a metal, preferable a transition metal, particularly a first row transition metal, with an oxidation state of +1 to +7, and R is —H, —OH, —CH$_3$, —O—CH$_3$, —F, —Cl, —Br, —C$_2$H$_5$ or a higher alkyl group, —OC$_2$H$_5$ or a higher alkoxy group, or a suitable inorganic counter anion. Particularly metal salts such as CuCl, NiSO$_4$, CoCl$_2$, MnCl$_2$ or VCl$_2$ are preferred.

Although it is preferred to introduce the peroxoacid, which is used as catalyst according to the invention, directly into the reaction mixture to form the initiator in situ, the peroxoacid itself may also be formed in situ by the reaction of hydrogen peroxide with the oxoacid corresponding to the inventive peroxoacid.

In an alternative embodiment, the object of the invention is thus solved by the use of a mixture comprising hydrogen peroxide and an oxoacid as catalyst in the preparation of haloalkanesulfonic acids from haloalkanes and sulfur trioxide, especially in the preparation of trifluoromethanesulfonic acid from trifluoromethane and sulfur trioxide. Optionally the mixture may comprise a solvent.

The oxoacid used in the mixture according to the invention must be suitable to yield a stable peroxoacid upon the reaction with hydrogen peroxide. In this alternative embodiment, the catalyst compound is produced in situ in the reaction mixture.

The oxoacid may be a monoprotic or a polyprotic acid. As monoprotic acids, alkanesulfonic acids may be employed in the mixture. Upon reaction with hydrogen peroxide, a catalyst corresponding to formula (I) is formed in situ from the alkanesulfonic acid.

Particularly, if a polyprotic acid is used, only a part of the hydroxyl groups may be replaced by peroxy groups upon the reaction with hydrogen peroxide. Preferably, polyprotic oxoacids of boron, silicon, phosphorus and/or sulfur, boric acid (H$_3$BO$_3$) and/or phosphoric acid (H$_3$PO$_4$) are used in a mixture according to the invention.

In a preferred embodiment, any of the aforementioned mixtures may comprise a compound M-R, wherein M is a metal, preferable a transition metal, particularly a first row transition metal, with an oxidation state of +1 to +7, and R is —H, —OH, —CH$_3$, —O—CH$_3$, —F, —Cl, —Br, —C$_2$H$_5$ or a higher alkyl group, —OC$_2$H$_5$ or a higher alkoxy group, or a suitable inorganic counter anion. Particularly metal salts such as CuCl, NiSO$_4$, CoCl$_2$, MnCl$_2$ or VCl$_2$ are preferred.

In an alternative embodiment, the object of the invention is solved by a process for the preparation of haloalkanesulfonic acids from haloalkanes and sulfur trioxide comprising the steps of
 i) providing sulfur trioxide;
 ii) reacting the sulfur trioxide with a haloalkane, especially trifluoromethane, in a high-pressure autoclave or laboratory reactor;
 iii) setting a pressure of from 1 to 200 bar;
 iv) introducing a stable peroxoacid as defined above as catalyst or an initiator as defined above
 v) controlling the temperature of the reaction mixture at 0° C. to 100° C.;
 vi) if necessary purifying the reaction product, for example, by distillation or extraction.

The stable peroxoacid which may be employed in step iv) corresponds to the peroxoacid which is described above to be used as catalyst in the preparation of haloalkanesulfonic acids. Alternatively, an isolated initiator as described above, i.e., the activated reaction product of a peroxoacid and sulfur trioxide, may be introduced into the reaction mixture.

In a preferred embodiment, a compound M-R can be additionally introduced in step iv, wherein M is a metal, preferable a transition metal, particularly a first row transition metal, with an oxidation state of +1 to +7, and R is —H, —OH, —CH$_3$, —O—CH$_3$, —F, —Cl, —Br, —C$_2$H$_5$ or a higher alkyl group, —OC$_2$H$_5$ or a higher alkoxy group, or a suitable inorganic counter anion. Particularly metal salts such as CuCl, NiSO$_4$, CoCl$_2$, MnCl$_2$ or VCl$_2$ are preferred.

Surprisingly, it was found that working at temperatures well below 100° C. enables the production of haloalkanesulfonic acids with high yields and low amount of impurities. Therefore, the temperature at which the reaction between the educts takes place is preferably 80° C. or below, especially 70° C. or below, especially preferred 60° C. or below or 55° C. or below. The reaction also runs at 0° C., but, of course, needs longer reaction time compared to higher temperatures. The temperature is therefore preferably about room temperature, especially it is 20° C. or above, preferably 25° C. or above, preferred 30° C. or above. Thus, working in a temperature range of from 35° C. to 65° C. is preferred. Especially preferred is a temperature range of from 40° C. to 60° C., preferably from 45° C. to 55° C. Surprisingly it was found that working at these comparably low temperatures of 60° C. or below and preferably around 45° C. to 55° C. enables the production of sulfonic acids with low amount of side products.

Sulfur trioxide may be provided in the form of oleum, i.e., a solution of sulfur trioxide in sulfuric acid. Instead of oleum also pure sulfur trioxide can be employed. This avoids the preparation of sulfur trioxide solutions. The reaction conditions are here without added solvents. Further, non-reacted sulfur trioxide can evaporate, avoiding the necessity of quenching it.

In a further embodiment, sulfur trioxide is used in a form of oleum with a sulfur trioxide content of 50% (w/w) or less, or 65% (w/w) or more. Surprisingly it has been found that for the processes of the present invention also oleum with a sulfur trioxide content of 65% (w/w) or more, especially of 70% w/w or more can be used without negatively affecting the inventive process. Even pure sulfur trioxide (100% (w/w) sulfur trioxide) may be used.

Due to the advantages being connected with the use of pure sulfur trioxide mentioned above, the use of pure sulfur trioxide is preferred in the process for manufacturing haloalkanesulfonic acids according to the present invention. As contrary to the prior art, a circulation of solvent is not necessary, haloalkanes comprising higher amounts of impurities compared to the prior art can be used. Impurities usually are enriched in the solvent leading to a reduced yield of haloalkanesulfonic acids. By avoiding solvents and thus a circulation of them, impurities originating from the haloalkanes are not negatively influencing the production of haloalkanesulfonic acids when pure sulfur trioxide is employed.

Sulfur trioxide, especially pure sulfur trioxide is reacted with a haloalkane in a reactor. For haloalkanes with a low boiling point, the use of a high-pressure reactor is necessary. As an example, for perfluorocyclohexane (51° C. sublimes), perfluoro(methyl)cyclohexane (bp. 76° C.) and perfluorodecalin (bp. 142° C.), a common laboratory reactor is sufficient. In the case of gaseous haloalkanes, for example, trifluoromethane, a pressure of 1 to 200, preferably 1 to 50 bar or preferably to 46 bar, gas pressure is set.

Subsequently, the peroxoacid catalyst according to the present invention may be added. The catalyst may be provided in pure form or dissolved in a suitable solvent. Preferably, the initial molar ratio between the catalyst and SO$_3$ is in the range of 1:50 to 1:10000, more preferably 1:100 to 1:500, particularly 1:150. The catalyst may be provided in a solvent, particularly in sulfuric acid. The same molar ratio applies, when in an alternative embodiment of the inventive process, the inventive isolated initiator is added.

After the reaction has taken place, the reaction mixture contains essentially of the respective haloalkanesulfonic acid, especially trifluoromethanesulfonic acid, as well as sulfuric acid. This mixture of haloalkanesulfonic acid, especially trifluoromethanesulfonic acid (TFMS), and $H_2SO_4$ might afterwards be used as the respective mixture. The combination of a haloalkanesulfonic acid, especially trifluoromethanesulfonic acid, and sulfuric acid provides a strong acid in which even gold might be solubilized enabling different fields of technical applicability.

Alternatively, the trifluoroalkanesulfonic acid, especially TFMS, might be separated i.e. the method of the invention comprises the optional step of the purifying the reaction product, which might be done by distillation or extraction.

In an alternative embodiment, the object of the invention is solved by a process for the preparation of haloalkanesulfonic acids from haloalkanes and sulfur trioxide comprising the steps of
  i) providing sulfur trioxide;
  ii) reacting the sulfur trioxide with a haloalkane, especially trifluoromethane, in a high-pressure autoclave or laboratory reactor;
  iii) setting a pressure of from 1 to 200 bar;
  iv) introducing a mixture comprising hydrogen peroxide and an oxoacid, as defined above, wherein the compounds of the mixture are introduced sequentially or simultaneously;
  v) controlling the temperature of the reaction mixture at 0° C. to 100° C.;
  vi) if necessary purifying the reaction product, for example, by distillation or extraction.

The process according to this embodiment of the invention differs from the aforementioned embodiment of the inventive process in that the catalyst is employed by introducing an oxoacid and hydrogen peroxide rather than a peroxoacid. The peroxoacid is thus formed in situ in the autoclave or laboratory reactor in which the reaction of sulfur trioxide and the haloalkane takes place.

Any suitable oxoacid which can be used in a catalyst mixture in the preparation of haloalkanesulfonic acids as defined above can be employed. Accordingly, the oxoacid needs to be capable of forming a stable peroxoacid.

Particularly, a monoprotic acid, especially an alkanesulfonic acid, may be chosen as oxoacid. Alternative suitable oxoacids comprise oxoacids of boron, silicon, phosphorus and/or sulfur. The oxoacid may be a monoprotic or a polyprotic acid. Particularly, if a polyprotic acid is used, only a part, especially only one, of the hydroxyl groups may be replaced by peroxy groups upon the reaction with hydrogen peroxide. Preferably, boric acid ($H_3BO_3$) and/or phosphoric acid ($H_3PO_4$) are employed.

Both the oxoacid and hydrogen peroxide are added to the reactor. They can be added in a mixture, optionally with a solvent. Suitable solvents comprise sulfuric acid or a liquid alkanesulfonic acid, e.g. methanesulfonic acid. The oxoacid and the peroxide may also be added separately but simultaneously. If both compounds are added separately, each may optionally be dissolved in a solvent, for example sulfuric acid. In yet another alternative, both compounds may be added sequentially, wherein each compound may be added as the first or the second compound.

Preferably, the oxoacid and hydrogen peroxide are added in a molar ratio of 1:5 to 5:1, more preferably in a molar ratio of 1:2 to 2:1, most preferably in a molar ratio of 1:1.

The initial molar ratio between the oxoacid and the $SO_3$ is preferably in the range of 1:50 to 1:10000, more preferably in the range of 1:100 to 1:500.

In a preferred embodiment, the mixture introduced in step iv) may comprise a compound M-R, wherein M is a metal, preferable a transition metal, particularly a first row transition metal, with an oxidation state of +1 to +7, and R is —H, —OH, —$CH_3$, —O—$CH_3$, —F, —Cl, —Br, —$C_2H_5$ or a higher alkyl group, —$OC_2H_5$ or a higher alkoxy group, or a suitable inorganic counter anion. Particularly metal salts such as CuCl, $NiSO_4$, $CoCl_2$, $MnCl_2$ or $VCl_2$ are preferred.

In an alternative embodiment, the object of the invention is solved by a mixture comprising a haloalkane, sulfur trioxide, a peroxoacid stable at room temperature and optionally a solvent. The inventive mixture is capable of producing a haloalkanesulfonic acid. Particularly, if the mixture is set at a pressure of 1 to 100 bar and held at a temperature of 0 to 100° C., a haloalkanesulfonic can be produced in an efficient way. The stable peroxoacid acts as a catalyst. In a preferred embodiment, the haloalkane is trifluoromethane. Such a preferred mixture is capable of forming trifluoromethanesulfonic acid.

In an alternative embodiment, the object of the invention is solved by a mixture comprising a haloalkane, sulfur trioxide, an initiator as defined above and optionally a solvent. The inventive mixture is capable of producing a haloalkanesulfonic acid. Particularly, if the mixture is set at a pressure of 1 to 100 bar and held at a temperature of 0 to 100° C., a haloalkanesulfonic can be produced in an efficient way. The stable peroxoacid acts as a catalyst. In a preferred embodiment, the haloalkane is trifluoromethane. Such a preferred mixture is capable of forming trifluoromethanesulfonic acid.

In a preferred embodiment, the mixture may comprise a compound M-R, wherein M is a metal, preferable a transition metal, particularly a first row transition metal, with an oxidation state of +1 to +7, and R is —H, —OH, —$CH_3$, —O—$CH_3$, —F, —Cl, —Br, —$C_2H_5$ or a higher alkyl group, —$OC_2H_5$ or a higher alkoxy group, or a suitable inorganic counter anion. Particularly metal salts such as CuCl, $NiSO_4$, $CoCl_2$, $MnCl_2$ or $VCl_2$ are preferred.

In an alternative embodiment, the object of the invention is solved by a mixture comprising a haloalkane, sulfur trioxide an oxoacid, hydrogen peroxide and optionally a solvent, wherein the oxoacid is capable of forming a stable inorganic peroxoacid. Preferably, an alkanesulfonic acid or an inorganic oxoacid of boron, silicon, phosphorus or sulfur may be employed as oxoacid.

The inventive mixture is capable of producing a haloalkanesulfonic acid. Particularly, if the mixture is set at a pressure of 1 to 100 bar and held at a temperature of 0 to 100° C., a haloalkanesulfonic can be produced in an efficient way. The inorganic oxoacid and the hydrogen peroxide react in situ to form an inorganic stable peroxoacid, which is capable of acting as catalyst.

In a preferred embodiment, the haloalkane is trifluoromethane. Such a preferred mixture is capable of forming trifluoromethanesulfonic acid.

In a preferred embodiment, the mixture may comprise a compound M-R, wherein M is a metal, preferable a transition metal, particularly a first row transition metal, with an oxidation state of +1 to +7, and R is —H, —OH, —$CH_3$, —O—$CH_3$, —F, —Cl, —Br, —$C_2H_5$ or a higher alkyl group, —$OC_2H_5$ or a higher alkoxy group, or a suitable

EXAMPLES

Example 1

Representative Procedure for the Preparation of Triflic Acid

In a 4 L stainless steel high-pressure reactor, 1.789 kg of fuming sulfuric acid (34.9%) and 285 g of fluoroform ($CHF_3$) were added. The total pressure inside the reactor reached 30.7 bar. The reactor was heated to 50° C. with a constant stirring speed of 360 rpm. The pre-catalyst consists of a mixture of 71.38 mmoles of hydrogen peroxide (60%), 90 mL sulfuric acid (98%) and 0.1532 moles of MSA (99.5%). The pre-catalyst was added against the internal pressure of the reactor using a HPLC pump connected to a cooling system to maintain the pre-catalyst at 0° C. The mixture was allowed to react for 24 h and then a sample was taken and further analyzed by $^{19}F$ NMR. Integration against an internal standard revealed 10% yield of triflic acid and high quantities of dissolved fluoroform. Triflic acid can be easily distilled from the reaction mixture taking advantage of the different boiling points of the components.

Example 2

Representative Procedure for the Preparation of Triflic Acid

In a 4 L stainless steel high-pressure reactor, 1.805 kg of fuming sulfuric acid (34.9%) and 271 g of fluoroform ($CHF_3$) were added. The internal pressure of the reactor increased to 31 bar. The reactor was heated to 50° C. with constant stirring speed of 360 rpm. The pre-catalyst consists of a mixture of 71.38 mmoles of hydrogen peroxide (60%), 90 mL sulfuric acid (98%) and 0.1532 moles of MSA (99.5%). A co-additive was used consisting of 771 mg of CuCl dissolved in a mixture of 1:10 $H_2SO_4$ and MSA. The pre-catalyst mixture and the co-catalyst are added into the reactor using a HPLC pump. After 24 h of reaction time, an aliquot is extracted using a reduce pressure sampling system The sample was analyzed by $^{19}F$ NMR, integration against an internal standard showed the formation of triflic acid in 12% yield.

The invention claimed is:

1. A method of preparing a haloalkanesulfonic acid comprising:
   reacting sulfur trioxide with at least one peroxoacid or a salt thereof, wherein the peroxoacid is stable at room temperature to create an activated form of sulfur trioxide; and
   reacting the activated form of sulfur trioxide with a haloalkane at a temperature of 60° C. or below to form a haloalkanesulfonic acid.

2. The method of claim 1, wherein the haloalkane is trifluoromethane and the haloalkanesulfonic acid is trifluoromethanesulfonic acid.

3. The method of claim 1, wherein the at least one peroxoacid comprises a compound of formula (I)

ALK-$SO_2$—O—O—X      (I), wherein

ALK is selected from the group consisting of branched alkyl, halogenated branched alkyl, unbranched alkyl, and halogenated unbranched alkyl; and X is selected from the group consisting of hydrogen, zinc, aluminium, an alkali earth metal, and an alkaline earth metal.

4. The method of claim 3, wherein ALK is selected from the group consisting of methyl, ethyl, propyl, butyl, isopropyl, isobutyl group, and halogenated forms thereof.

5. The method of claim 3, wherein X is hydrogen.

6. The method of claim 1, wherein the peroxoacid comprises at least one inorganic peroxoacid.

7. The method of claim 6, wherein the peroxoacid is a peroxoacid of boron, silicon, phosphorus, sulfur, or a salt thereof.

8. The method of claim 6, wherein the peroxoacid is made by reaction of an oxoacid with a peroxide.

9. The method of claim 8, wherein the peroxide is hydrogen peroxide.

10. A method of preparing a haloalkanesulfonic acid comprising:
    reacting a haloalkane and sulfur trioxide at a temperature of 60° C. or below and using at least one initiator of formula (III):

ALK-$SO_2$—O—O—$SO_2$—OX      (III), wherein

ALK is selected from the group consisting of branched alkyl, halogenated branched alkyl, unbranched alkyl, and halogenated unbranched alkyl; and X is selected from the group consisting of hydrogen, zinc, aluminium, an alkali earth metal, and an alkaline-earth metal.

11. The method of claim 10, wherein the haloalkanesulfonic acid is trifluoromethanesulfonic acid.

12. The method of claim 10, wherein ALK is selected from the group consisting of methyl, ethyl, propyl, butyl, isopropyl, isobutyl group, and halogenated forms thereof.

13. The method of claim 10, wherein the initiator is made by reacting a peroxoacid or a salt thereof, that is stable at room temperature, with sulfur trioxide.

14. The method of claim 10, wherein the initiator is made by reacting an inorganic peroxoacid that is stable at room temperature, and selected from the group consisting of boron, silicon, phosphorus, sulfur, and a salt thereof, with sulfur trioxide.

15. A method of preparing a haloalkanesulfonic acid comprising:
    mixing hydrogen peroxide, an oxoacid, and optionally a solvent to form a catalytic mixture;
    reacting sulfur trioxide with the catalytic mixture to create an activated form of sulfur trioxide; and
    reacting the activated form of sulfur trioxide with a haloalkane at a temperature of 60° C. or below to form a haloalkanesulfonic acid.

16. The method of claim 15, wherein the haloalkane is trifluoromethane and the haloalkanesulfonic acid is trifluoromethanesulfonic acid.

17. The method of claim 15, wherein the oxoacid is a monoprotic acid or a polyprotic acid.

18. The method of claim 17, wherein
    the monoprotic acid is an alkanesulfonic acid; and
    the polyprotic acid is boric acid, phosphoric acid, or an oxoacid of one or more of boron, silicon, and phosphorus.

19. The method of claim 1, further comprising using a compound M-R, wherein M is a metal, and R is selected from the group consisting of H, OH, CH₃, OCH₃, F, Cl, Br, alkyl, alkoxy, and an inorganic counter anion.

20. The method of claim 19, wherein M is a transition metal.

21. The method of claim 20, wherein M is a first row transition metal, with an oxidation state of +1 to +7.

22. A process for the preparation of haloalkanesulfonic acids from haloalkanes and sulfur trioxide comprising the steps of:
   i) providing sulfur trioxide;
   ii) reacting the sulfur trioxide with a haloalkane in a high-pressure autoclave or laboratory reactor;
   iii) setting a pressure of from 1 to 200 bar;
   iv) introducing
      a) a peroxoacid of formula (I)

ALK-SO₂—O—O—X    (I), wherein
      ALK is selected from the group consisting of branched alkyl, halogenated branched alkyl, unbranched alkyl, and halogenated unbranched alkyl; and
      X is selected from the group consisting of hydrogen, zinc, aluminium, an alkali earth metal, and an alkaline earth metal;
      or
      b) an initiator of of formula (III):

ALK-SO₂—O—O—SO₂—OX    (III), wherein
      ALK selected from the group consisting of branched alkyl, halogenated branched alkyl, unbranched alkyl, and halogenated unbranched alkyl; and
      X is selected from the group consisting of hydrogen, zinc, aluminium, an alkali earth metal, and an alkaline earth metal;
   v) controlling the temperature of the reaction mixture at 0° C. to 60° C.; and
   vi) optionally, purifying the reaction product by distillation or extraction.

23. A process for the preparation of haloalkanesulfonic acids from haloalkanes and sulfur trioxide comprising the steps of
   i) providing sulfur trioxide;
   ii) reacting the sulfur trioxide with a haloalkane in a high-pressure autoclave or laboratory reactor;
   iii) setting a pressure of from 1 to 200 bar;
   iv) introducing a mixture of hydrogen peroxide, an oxoacid, and optionally a solvent, wherein the compounds of the mixture are introduced sequentially or simultaneously
   v) controlling the temperature of the reaction mixture at 0° C. to 60° C.; and
   vi) optionally, purifying the reaction product by distillation or extraction.

* * * * *